(12) United States Patent
Wu et al.

(10) Patent No.: US 10,894,930 B2
(45) Date of Patent: Jan. 19, 2021

(54) TRACTION FLUID WITH IMPROVED LOW TEMPERATURE PROPERTIES

(71) Applicant: VALVOLINE LICENSING AND INTELLECTUAL PROPERTY LLC, Lexington, KY (US)

(72) Inventors: Gefei Wu, Lexington, KY (US); Rajkumar Rajule, Kalyan West (IN); Ning Ren, Naperville, IL (US); Jesse Dambacher, Lexington, KY (US); Frances Lockwood, Georgetown, KY (US)

(73) Assignee: VALVOLINE LICENSING AND INTELLECTUAL PROPERTY LLC, Lexington, KY (US)

( * ) Notice: Subject to any disclaimer, the term of this patent is extended or adjusted under 35 U.S.C. 154(b) by 0 days.

(21) Appl. No.: 16/817,893

(22) Filed: Mar. 13, 2020

(65) Prior Publication Data

US 2020/0291322 A1 Sep. 17, 2020

Related U.S. Application Data

(60) Provisional application No. 62/817,732, filed on Mar. 13, 2019.

(51) Int. Cl.
*C10M 177/00* (2006.01)
*C07C 5/10* (2006.01)
(Continued)

(52) U.S. Cl.
CPC ............. *C10M 105/02* (2013.01); *C07C 5/10* (2013.01); *C10M 177/00* (2013.01);
(Continued)

(58) Field of Classification Search
CPC .............. C10M 105/02; C10M 177/00; C10M 2203/045; C10M 105/04; C07C 5/10;
(Continued)

(56) References Cited

U.S. PATENT DOCUMENTS 3,577,361 A * 5/1971 Hammann ............... C07C 15/12
252/73
3,925,217 A * 12/1975 Green ................. F16C 33/6688
508/463

(Continued)

FOREIGN PATENT DOCUMENTS

EP 0748863 A2 * 12/1996 ........ C10M 171/002
EP 0748863 A2 12/1996
(Continued)

OTHER PUBLICATIONS

International Search Report and Written Opinion issued in PCT application No. PCT/US2020/022559, dated Jul. 7, 2020.

*Primary Examiner* — Pamela H Weiss
(74) *Attorney, Agent, or Firm* — Benesch, Friedlander, Coplan & Aronoff LLP

(57) ABSTRACT

A traction fluid comprising a blend of 2,3-dicyclohexyl-2,3-dimethylbutane (HAD) and 2,3-dicyclohexyl-2,3-dimethylbutane (iso-HAD) is found to have a lower viscosity at low temperatures when compared to a traction fluid having only HAD or only iso-HAD as a base fluid with no compromise to traction coefficient. The traction fluid may comprise additives. The traction fluid usually comprises HAD:iso-HAD between about 8:1 to about 1:3. Further, the HAD: iso-HAD traction fluid blend is produced by a method of simultaneous co-production of hydrogenated HAD and hydrogenated iso-HAD from an alpha styrene dimer and an iso-HAD precursor with a yield of about 90% in a method that does not require a purification step.

11 Claims, 4 Drawing Sheets

(51) Int. Cl.
  *C10N 20/00* (2006.01)
  *C10N 30/02* (2006.01)
  *C10N 30/18* (2006.01)
  *C10N 40/04* (2006.01)
  *C10M 105/02* (2006.01)
  *C10N 70/00* (2006.01)

(52) U.S. Cl.
  CPC ...... *C07C 2521/18* (2013.01); *C07C 2523/46* (2013.01); *C07C 2601/14* (2017.05); *C10M 2203/045* (2013.01); *C10N 2020/065* (2020.05); *C10N 2030/02* (2013.01); *C10N 2030/18* (2013.01); *C10N 2040/045* (2020.05); *C10N 2040/046* (2020.05); *C10N 2070/00* (2013.01)

(58) Field of Classification Search
  CPC ............ C07C 2523/46; C07C 2521/18; C07C 2601/14; C10N 2070/00; C10N 2030/18; C10N 2030/02; C10N 2020/065; C10N 2040/046; C10N 2040/045; C10N 2030/06; C10N 2020/02
  See application file for complete search history.

(56) References Cited

U.S. PATENT DOCUMENTS

| | | | |
|---|---|---|---|
| 3,975,278 A * | 8/1976 | Wygant | C10M 171/002 476/7 |
| 3,994,816 A * | 11/1976 | Wygant | C10M 105/04 252/73 |
| 4,556,503 A * | 12/1985 | Tsubouchi | C10M 105/04 252/73 |
| 4,684,754 A * | 8/1987 | Tsubouchi | C10M 105/02 585/21 |
| 4,704,490 A * | 11/1987 | Tsubouchi | C10M 105/02 585/1 |
| 4,889,649 A * | 12/1989 | Murai | C10M 105/02 252/73 |
| 4,975,215 A | 12/1990 | Kazuaki et al. | |
| 5,171,918 A | 12/1992 | Shubkin et al. | |
| 5,422,027 A | 6/1995 | Abe et al. | |
| 6,319,879 B1 * | 11/2001 | Yoshida | C10M 171/002 508/110 |
| 6,320,088 B1 | 11/2001 | Matsuno et al. | |
| 6,372,696 B1 | 4/2002 | Tipton | |
| 6,730,640 B2 | 5/2004 | Sowerby et al. | |
| 7,402,715 B2 | 7/2008 | Yoshida et al. | |
| 7,504,667 B2 | 3/2009 | Fujikura et al. | |
| 7,629,303 B2 | 12/2009 | Hagemeister et al. | |
| 7,964,540 B2 | 6/2011 | Yoshida et al. | |
| 8,252,735 B2 | 8/2012 | Hagemeister et al. | |
| 8,637,438 B2 | 1/2014 | Yamada | |
| 9,296,973 B2 | 3/2016 | Fu et al. | |
| 2004/0152607 A1 | 8/2004 | Chapaton et al. | |
| 2004/0152931 A1 | 8/2004 | Chapaton et al. | |
| 2004/0242441 A1 | 12/2004 | Chiu | |
| 2005/0121360 A1 | 6/2005 | Lange et al. | |
| 2007/0042915 A1 * | 2/2007 | Yoshida | C07C 13/605 508/110 |
| 2010/0048434 A1 * | 2/2010 | Hagemeister | C10M 111/02 508/110 |

FOREIGN PATENT DOCUMENTS

| | | |
|---|---|---|
| JP | 05-001292 A | 1/1993 |
| JP | 2001342477 A * | 12/2001 |
| JP | 2009-067961 A | 4/2009 |

* cited by examiner

TRACTION FLUID WITH IMPROVED LOW TEMPERATURE PROPERTIES

PRIORITY DATA

This application claims priority to U.S. Provisional Patent Application No. 62/817,732, filed Mar. 13, 2019, herein incorporated by reference in its entirety.

FIELD OF INVENTION

The present disclosure generally relates to a traction fluid blend for an IVT with improved viscosity at low temperatures. Also disclosed, a method of simultaneously hydrogenating a blend of molecules to produce a traction fluid base oil.

BACKGROUND

Traction fluids rely on its high shear strength to provide torque transmission in devices like continuous variable transmission (CVT) or infinite variable transmission (IVT). Such transmission allows seamless integration with internal combustion engine for optimal engine performance and maximum fuel efficiency. In the year 1999, toroidal continuous variable transmission (T-CVT) cars were introduced in the market and the traction fluid used for T-CVT requires high level of performance in terms of high traction coefficient and low temperature fluidity of the fluid.

SUMMARY

The surprising and non-obvious discovery that iso-HAD, a molecule that by itself is solidified at low temperatures can improve the fluidity of a HAD:iso-HAD blend at low temperatures will now be described.

A traction fluid that provides improved fluidity as a low temperature is a blend of:

Formula I:

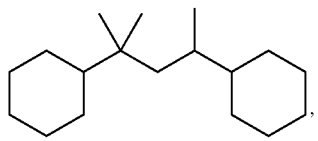

Formula II:

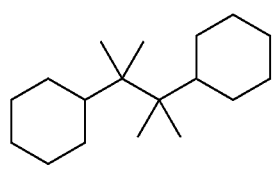

and one or more additives.

The traction fluids that are a blend have improved properties of lower viscosities at low temperatures with no effect on overall traction coefficient of the fluid.

Methods of making a traction fluid blend stock are also provided. The methods have the advantage of simultaneously hydrogenating a HAD precursor and an iso-HAD precursor in a reaction vessel such that the reaction product requires no purification and instantly contains HAD and iso-HAD in a preferred mix ratio. The reaction product that is a blend of HAD and iso-HAD that may then be combined with additives to form a finished traction fluid.

In the methods, the HAD precursor serves not only as reactant but also solvent for the iso-HAD precursor.

Other fluids, methods, features and/or advantages is, or will become, apparent upon examination of the following FIGs and detailed description. It is intended that all such additional fluids, methods, features, and advantages be included within this description and be protected by the accompanying claims.

BRIEF DESCRIPTION OF THE DRAWINGS

In the accompanying figures, chemical formulas, chemical structures, and experimental data are given that, together with the detailed description provided below, describe example embodiments.

DETAILED DESCRIPTION

Figure 1:
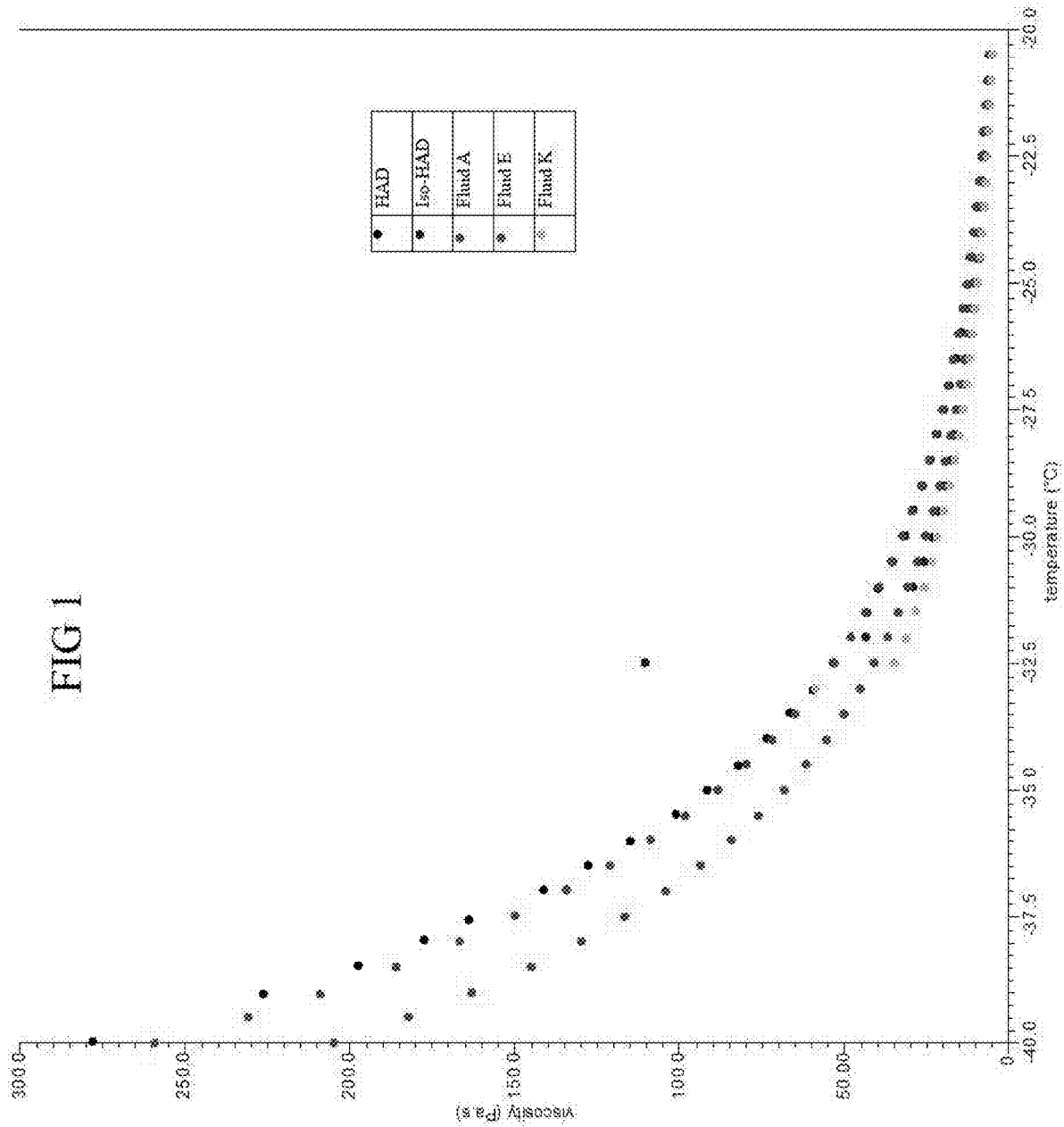
FIG. 1 is a graph demonstrating viscosity changes as temperature changes for fluids of different compositions.

The traction fluid blend will be described in detail.

HAD

Tsubouchi et al. (Lubrication Science 2004, 16(4), 393-403) reported parameters for designing molecular structure with high traction coefficient including high molecular stiffness, large size, short alkylene chain length, high melting point and low molecular polarity for getting good traction coefficient. The industry uses specially designed traction fluid such as hydrogenated alpha dimethyl styrene (HAD), which has excellent traction coefficient and low temperature viscosity-key performance parameters including: Melting point $-30°$ C., boiling point $112°$ C. (0.7 mm of Hg). The traction coefficient of HAD is reported as 0.058 at $140°$ C., with slide to roll ratio of 5% and maximum Hertz pressure of 1.1 GPa (*Japanese Journal of Tribology* Vol 38, 3, 1993). The chemical structure of HAD (CAS 38970-72-8; 2,4-dicyclohexyl-2-methylpentane) is presented in Formula I:

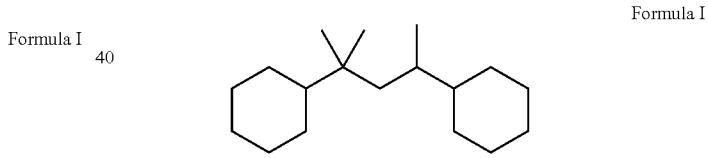

IsoHAD

The chemical structure of isoHAD (CAS 5171-88-0; 2,3-dicyclohexyl-2,3-dimethylbutane) is presented in Formula II:

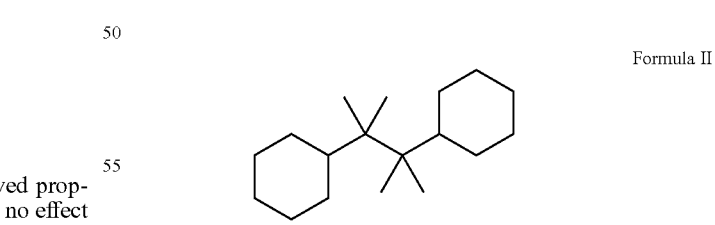

HAD/isoHAD Blends

Table 1 compares properties of Formula I and Formula II.

| | Formula I (HAD) | Formula II (isoHAD) |
|---|---|---|
| Kinematic Viscosity @ 40° C. (cSt) | 19.95 | 28.87 |
| Kinematic Viscosity @ 100° C. (cSt) | 3.56 | 4.7 |

-continued

|  | Formula I (HAD) | Formula II (isoHAD) |
| --- | --- | --- |
| Viscosity Index | 16 | 65 |
| Brookfield viscosity @−30° C. (cP) | 29,000 | Frozen |
| Pour Point (° C.) | −30 | −12 |
| Traction coefficient @ 90 C., 5% SRR, 1.25 GPa | 0.0995 | 0.1001 |

Additives

The traction fluid may comprise, in addition to a blend of Formula I and II, additives. Any additive that may improve the properties or functioning of the traction fluid may be added. The traction fluid may also comprise additives in an amount greater than about 0.01 (w/w) % and less than about 20 (w/w) %. The amount of any one additive may be in an amount between 0.01 (w/w) % and less than about 20 (w/w) %. If more than one additive is added to the formulation, the total amount of additives present may be in an amount from 0.01 (w/w) % and less than about 20 (w/w) %. Alternatively, the amount 0.01 (w/w) % and less than about 20 (w/w) % may refer to the each additive present in the traction fluid.

The additive may comprise an antifoaming agent that may be present in an amount of about 0.1 (w/w) %. The antifoaming agent may be a mixture of organic acid ester and siloxane or a silicone based fluid. The traction fluid may contain one, two or more than two anti-foaming agents. The antifoaming agent may comprise any appropriate defoamer.

The traction fluid may also comprise a viscosity modifier. The viscosity modifier may be present in an amount between 0.1 (w/w) % to 10 (w/w) % depending on target viscosity of the finished fluid.

The traction fluid may include additional additives such as an additive package including antioxidant agents, antiwear agents, extreme pressure agents, detergents, dispersants, antifoamer, anti-rust agents, friction modifiers, corrosion inhibitors, viscosity modifiers. The additive package may be added in an amount greater than about 0.01 (w/w) % and less than about 20 (w/w) %. The additive amount may also be described by any single digit found in the range between about 0.01 (w/w) % and less than about 20 (w/w) %, such as 5 (w/w) % or 7.8 (w/w) %. The additive may comprise, may consist essentially of or consist of a single ingredient, such as one de-foaming agent. Alternatively, the additive may comprise, may consist essentially of or consist of a commercially available additive package. The additive may comprise, may consist essentially of or consist of a viscosity modifier. The additive may comprise, may consist essentially of or consist of a combination of a defoamer, viscosity modifier and a transmission additive package.

The traction fluid may further optionally comprise a transmission additive package. The transmission additive package may be added in an amount greater than about 0.01 (w/w) % and less than about 20 (w/w) %. The additive amount may also be described by any single digit found in the range between about 0.01 (w/w) % and less than about 20 (w/w) %, such as 5.7 (w/w) % or 9.0 (w/w) %.

A traction fluid may comprise a blend of the molecule of Formula I:

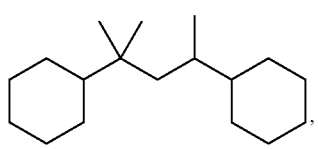

Formula I and
the molecule of Formula II:

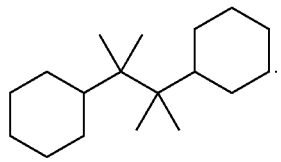

Formula II

The traction fluid that is a blend of Formula I and Formula II may also contain one or more additives selected from the group consisting of: anti-foaming agents, antioxidant agents, antiwear agents, extreme pressure agents, detergents, dispersants, anti-rust agents, friction modifiers, corrosion inhibitors, and viscosity modifiers.

All of the additives considered together may be present in an amount between about 0.01 (w/w) % and about 20 (w/w) % where the blend of Formula I and Formula II is present in an amount between about 80 (w/w) % and 99.99 (w/w) %.

The traction fluid may include one additive that is a defoaming agent in an amount of about 0.1 (w/w) %, a second additive that is a viscosity modifier in an amount of about 2 (w/w) %, and a third additive is a transmission additive package in an amount of about 5.7 (w/w) %. The additive may comprise, may consist essentially of or consist of a defoaming agent, a viscosity modifier and a transmission additive package.

The traction fluid may contain a blend of Formula I and Formula II in an amount between about 92 (w/w) % and about 94 (w/w) %.

The traction fluid may be described as follows. The amount of Formula I and Formula II relative to each other by may be defined by a mix ratio. The mix ratio, HAD:iso-HAD represents the amount of HAD (w/w) % relative to the isoHAD (w/w) %. Most preferably the mix ratio of HAD:iso-HAD is between 8:1 and 1:3. Even more preferably the mix ratio of HAD:isoHAD is between 1:1 and 1:3.

The traction fluids that are a blend of Formula I (HAD) and Formula II (iso-HAD) are characterized by: a viscosity that is lower than the viscosity of a traction fluid comprising Formula I or II as a base fluid alone; and/or a traction coefficient approximately equivalent to a traction fluid comprising Formula I or II as a base fluid alone.

The traction fluids that are a blend of Formula I and Formula II are characterized by: the viscosity of the a traction fluid blend being about 25 to 30% lower than the viscosity of a traction fluid comprising Formula I as a base fluid alone. In addition, the traction coefficient of the traction fluid blend is generally within about 1% of the traction coefficient of a traction fluid comprising Formula I as a base fluid alone. That is, the variation in the traction coefficient as measured does not vary from the traction coefficient of a traction fluid blend comprising only Formula I by greater than 1% of the traction coefficient value. Similarly, when a traction fluid HAD:isoHAD blend is compared to a traction fluid comprising HAD (Formula I), the variation in viscosity of the blend as measured by Brookfield viscosity @−30° C. (cP) does not vary by more than 30% when compared to fluids with HAD alone as base fluid. The traction fluids comprising only Formula II has un-measurable Brookfield viscosity @−30° C. as it freezes at that temperature, while its traction coefficient is slightly higher than the traction fluid of a blend of Formula I and Formula II.

Co-Synthesis of HAD and isoHAD

Inventors have previously disclosed a novel and scalable method for production of HAD from an alpha methyl styrene in U.S. patent application Ser. No. 16/214,867, filed Dec. 10, 2018.

Now a procedure for simultaneous co-hydrogenation of alpha dimethyl styrene dimer and an iso-HAD precursor that is scalable, economical, and safe will be described in detail. These procedures result in routinely greater than a 90% yield of a co-product.

The process can be summarized as follows:

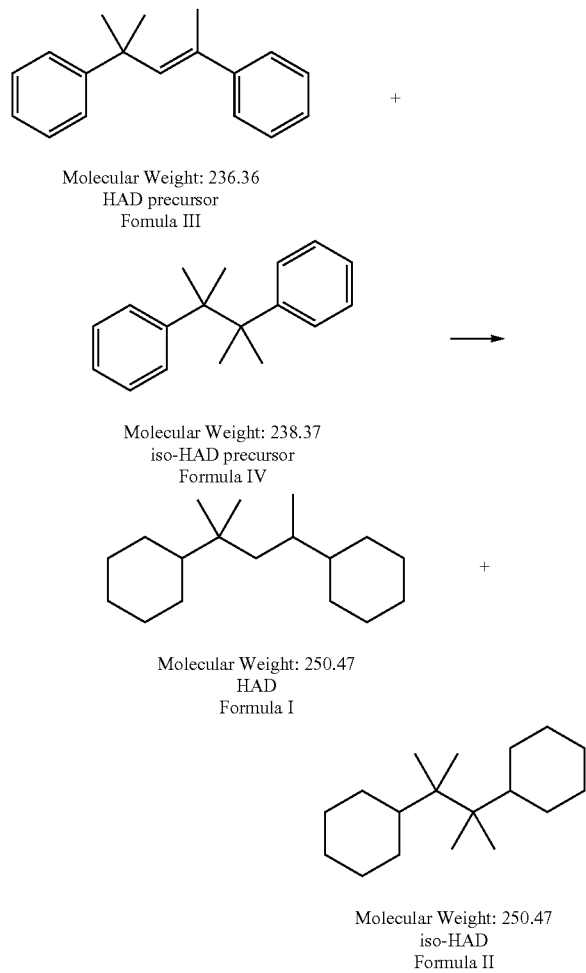

The methods of co-synthesis of HAD and iso-HAD require no purification step.

The methods of co-synthesis also provide a convenient method of preparing an iso-HAD precursor for hydrogenation because the HAD precursor, while being a reactant is additionally a solvent for the iso-HAD precursor.

The terms co-synthesis, co-production, co-products all refer to the fact that a HAD precursor and an iso-HAD precursor are added to a reactant vessel and both undergo a hydrogenation reaction simultaneously in the same reactant vessel.

The methods include adding to a Haste alloy reactor, with turbine impeller, under nitrogen a catalyst comprising Ru/C or Rh/C, an alpha dimethyl styrene dimer, and an iso-HAD precursor to form a reaction mixture. The reaction mixture is then heated under pressure until hydrogenation of the alpha dimethyl styrene dimer and of the iso-HAD precursor is complete. To recover the hydrogenated alpha dimethyl styrene dimer and iso-HAD, the reaction mixture is filtered through a celite bed under nitrogen to remove the catalyst. The catalyst may be recovered from the celite bed and recycled for use again in the method. This method of production is solventless or adds an amount of a protic solvent such as isopropyl alcohol. The reaction time varies from about 6 hours to 22 hours. The reaction time can be reduced by incresing the temperature and pressure.

The hydrogenation reaction may be monitored for completion by performing thin layer chromatography on a sample of the reaction mixture. The reaction is complete when hydrogen consumption ceases. Likewise, a sample of the reaction mixture may be analyzed by the absence of an aromatic peak in a nuclear magnetic resonance (NMR) spectra. Gas chromatograph mass spectrometry (GCMS) or any other technique may also be used to evaluate the completeness of the hydrogenation reaction.

Thus provided is a method for co-preparing HAD and iso-HAD comprising: adding to a reactor under nitrogen a catalyst comprising Ru/C or Rh/C; adding alpha dimethyl styrene dimer and an iso-HAD precursor to the reactor thereby forming a catalyst, alpha dimethyl styrene dimer, iso-HAD precursor reaction mixture; heating the reaction mixture under pressure until hydrogenation of the alpha dimethyl styrene dimer and the iso-HAD precursor is complete; and filtering the reaction mixture through a celite bed under nitrogen thereby obtaining a hydrogenated alpha dimethyl styrene dimer (HAD) and a hydrogenated iso-HAD (iso-HAD) co-product.

The reaction of the method of can proceed for about 6 to about 22 hours until completion. The heating of the method may include beginning with the formation of the reaction mixture in the reactor at ambient temperature and raising the temperature of the reaction mixture to about 110° C. or to about 125° C. until completion of the reaction. The reaction mixture in the reactor may be under a pressure of between about 14 and about 15 Kg/cm'. The reaction mixture in the reactor may be constantly stirred.

The method may also include a step of monitoring reaction completeness by testing the filtered hydrogenated alpha dimethyl styrene dimer product by nuclear magnetic resonance spectroscopy.

The method includes reaction conditions where the alpha methyl styrene dimer and iso-HAD precursor are added to the reaction mixture in equal amounts or where the ratio of alpha methyl styrene dimer:iso-HAD precursor are added to the reaction mixture is a ratio of between about 8:1 to about 1:3.

EXAMPLES

Example 1: Traction Fluid Blends of HAD and isoHAD

Compositions that blend of HAD (Formula I) and iso-HAD (Formula II) were made and are summarized in Table 2:

| Fluid | A | B | C | D | E | F | G | H | I | J | K |
|---|---|---|---|---|---|---|---|---|---|---|---|
| HAD:isoHAD | | 8:1 | 3:1 | 2:1 | 1:1 | 1:2 | 1:3 | 1:4 | 1:5 | 1:6 | |
| HAD | 92.2 | 82.2 | 69.5 | 62.13 | 46.78 | 31.23 | 23.56 | 18.85 | 15.7 | 11.72 | |
| iso-HAD | | 10 | 23.4 | 31.07 | 46.78 | 62.47 | 70.64 | 75.35 | 78.5 | 82.03 | 94.2 |

-continued

| Fluid | A | B | C | D | E | F | G | H | I | J | K |
|---|---|---|---|---|---|---|---|---|---|---|---|
| VM | 2 | 2 | 1.3 | 1 | 0.64 | 0.5 | | | | 0.45 | |
| DI | 5.7 | 5.7 | 5.7 | 5.7 | 5.7 | 5.7 | 5.7 | 5.7 | 5.7 | 5.7 | 5.7 |
| Defoamers | 0.1 | 0.1 | 0.1 | 0.1 | 0.1 | 0.1 | 0.1 | 0.1 | 0.1 | 0.1 | 0.1 |
| Total | 100 | 100 | 100 | 100 | 100 | 100 | 100 | 100 | 100 | 100 | 100 |
| KV100 (cSt) | 4.88 | 4.99 | 4.79 | 4.75 | 4.74 | 4.89 | 4.76 | 4.84 | 4.88 | 5.23 | 5.15 |
| KV40 (cSt) | 26.73 | 27.29 | 27.13 | 27.71 | 27.78 | 29.24 | 28.7 | 29.37 | 29.94 | 31.68 | 32.11 |
| Traction Coef. | 0.0942 | | | | 0.0948 | 0.0946 | 0.0947 | | | 0.0949 | 0.095 |
| BF −30 C. (cP) | 26,200 | 24,800 | 24,000 | 22,600 | 19,900 | 19,500 | 19,150 | 19,100 | 20,300 | frozen | frozen |
| BF −40 C. (cP) | 228,000 | | | | 164,800 | 162,500 | 158,200 | frozen | frozen | frozen | frozen |

In Table 2, the following abbreviations are used: HAD refers to Formula I; iso-HAD refers to Formula II, DI refers to a transmission additive package; VM refers to a viscosity modifier; KV100(cSt) and KV40 (cSt) refer to Kinematic Viscosity @100° C. and 40° C., respectively; Traction Coef. refers to Traction Coefficient @90° C., 5% SRR, 1.25 GPa; BF-30 (cP) and BF-40 (cP) refer Brookfield viscosity @−30° C. and −40° C. respectively.

Referring now to FIG. 1, the viscosity of Fluids A, E and K, a fluid that is 100% iso-HAD (no additives) and a fluid that is 100% HAD (no additives) as a function of temperature are shown. Fluid E, with a mix ratio of 1:1 has a lower viscosity than fluid A and improved viscosity over Fluid K, which is frozen at lower temperatures.

As can be seen in Table 2, the compositions contain the additives transmission additive package, defoamers and viscosity modifiers in amounts up to about 7.8 (w/w) % total. The amount of Formula I and Formula II are varied. The mix ratio of HAD:iso-HAD characterizes the amount of Formula I and Formula II to each other in the traction fluid composition. The traction coefficient were measured at 90° C. and pressure of 1.25 GPa under 5% slide to roll ratio. For Brookfield viscosity, 'frozen' indicates the viscosity is too high to measure when fluid freezes.

As can be seen in the Table 2, the traction coefficient increases slightly with increasing amounts of Formula II (iso-HAD) in the blend (compare traction coefficient of Fluid A (100% HAD) to fluids B-K). Not wishing to be bound by theory, but this is likely due to the fact that Formula I (HAD) has lower traction coefficient than Formula II (see Table I). However, Brookfield viscosity at −30° C. decreases with increasing concentration of iso-HAD and reaches a plateau at fluids E through I. The Brookfield viscosity at −30° C. increases at mix ratio of 1:6. The Brookfield viscosity at −40° C. increases at mix ratio of 1:4.

Most preferably, the formulations of Fluid E, F, and G, with a mix ratio of HAD:iso-HAD between 1:1 to 1:3 provide the optimal balance between performance (traction coefficient) and viscosity (Brookfield viscosity).

The traction fluids from blends of HAD and iso-HAD (Fluid B to J in Table 2) have lower low temperature viscosity than the traction fluids with HAD only (Fluid A) or iso-HAD only (Fluid K). Not wishing to be bound by theory, the reason behind this phenomena may be due to the fact that the viscosity of iso-HAD is actually lower than the viscosity of HAD before iso-HAD freezes, as it is demonstrated by rheometer test in FIG. 1 where sudden viscosity increase indicates freezing of the fluid.

The traction fluids from blend of HAD and iso-HAD have lower freezing point than iso-HAD while have lower viscosity than HAD.

Example 2: Co-Synthesis of HAD and isoHAD

In a one-liter Haste alloy reactor, with turbine impeller, a catalyst according to Table 3 was added. To the catalyst, isopropyl alcohol was added under nitrogen, in some of the examples. To the resultant catalytic solution, alpha dimethyl styrene dimer (AMS) and iso-HAD precursor was added. The reaction mixture was stirred with a stirrer at a constant rate of 700 RPM. The reaction mixture was heated to the temperature and pressure indicated in Table 3. Completion of the reaction was monitored by thin layer chromatography or NMR and when no more hydrogen consumption was indicated, the reaction mixture was filtered through a celite bed under nitrogen. The product was also analyzed by nuclear magnetic resonance (NMR). The yield was about 90-92%.

Figure 2A:
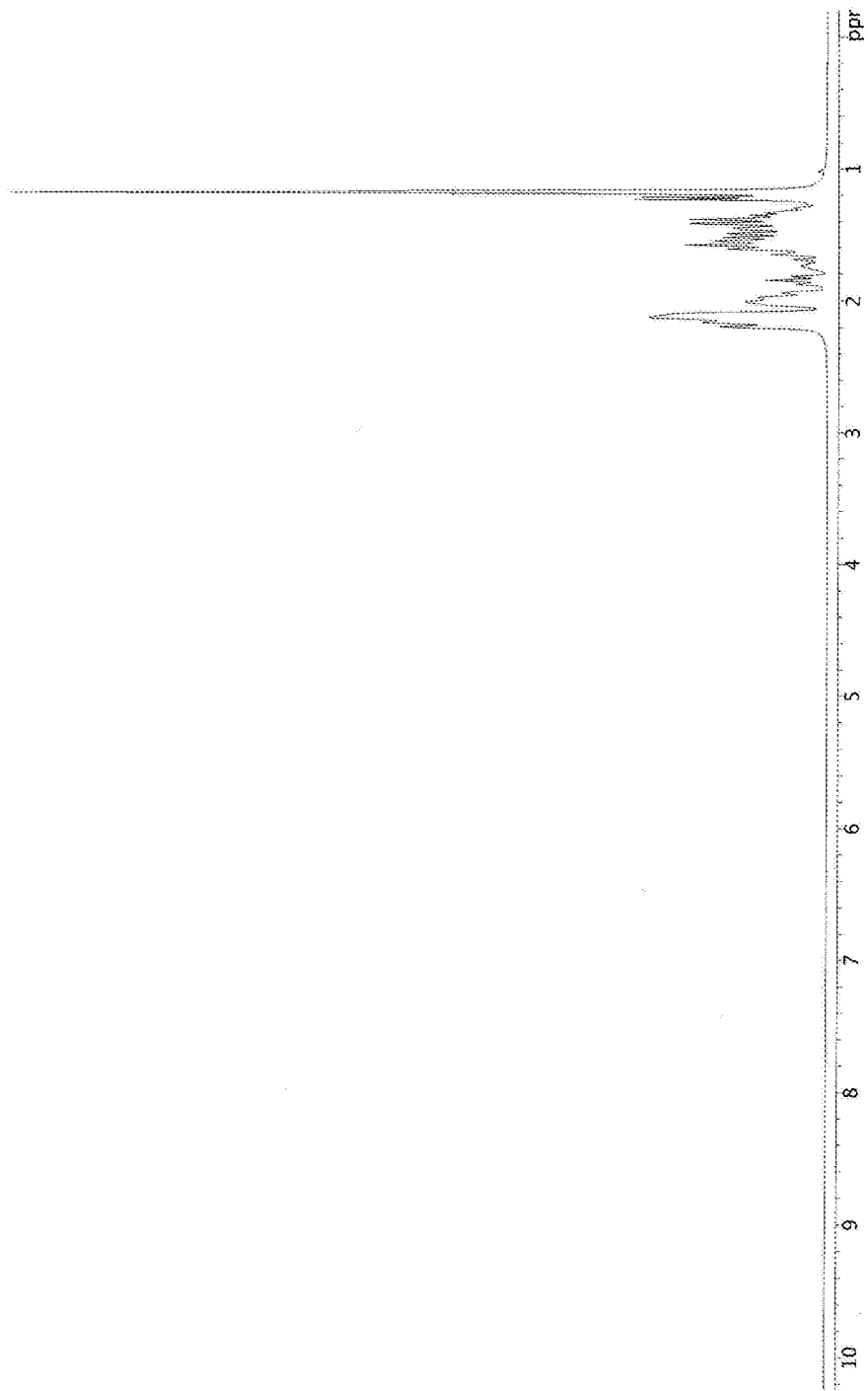
FIG. 2A-C shows the NMR spectra for co-produced hydrogenated alpha dimethyl styrene dimer and hydrogenated iso-HAD prepared according to the methods of the present disclosure.
Figure 2B:
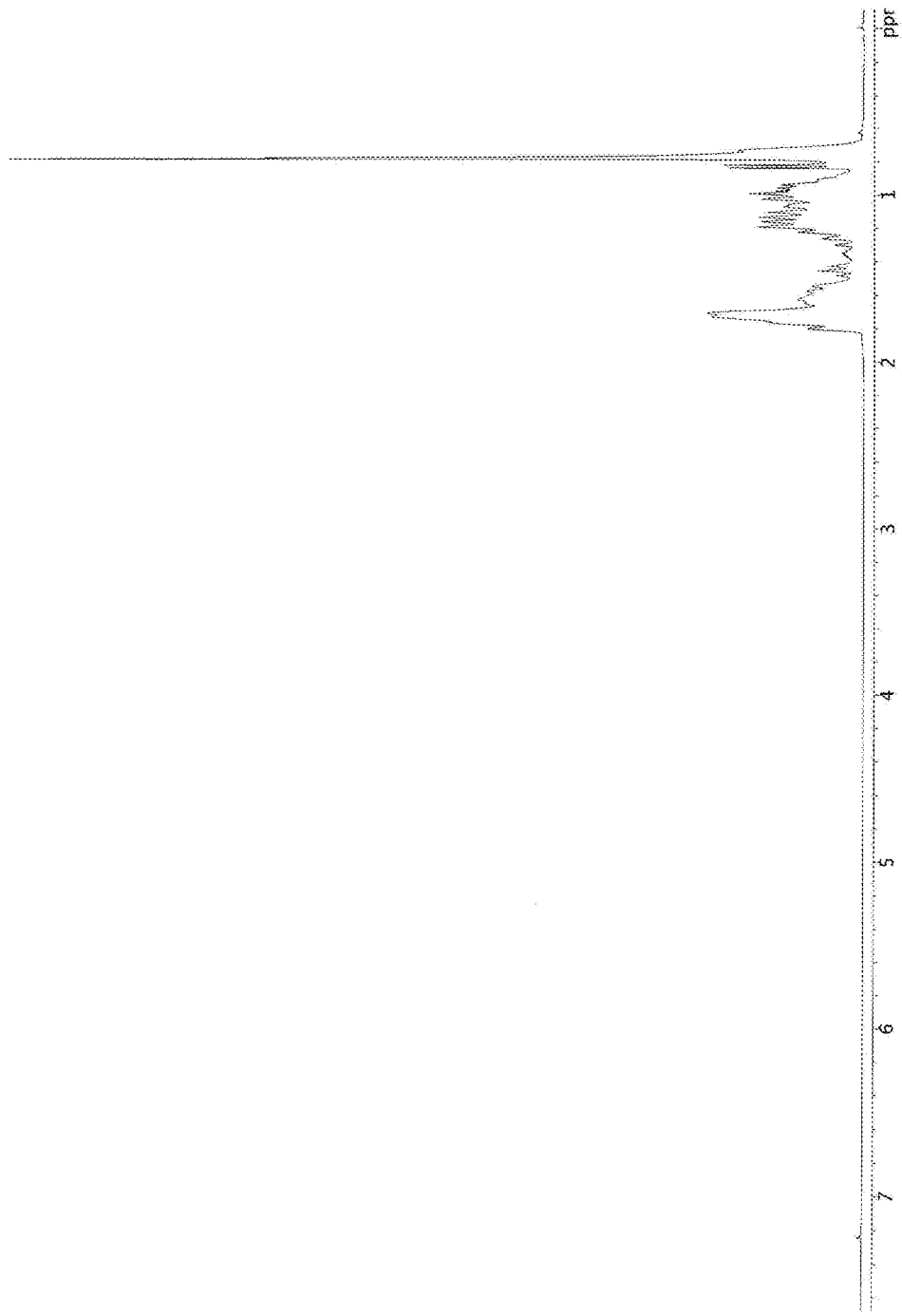

The results are shown in Table 3:

| AMS dimer (g) | Iso-HAD Precursor (g) | Solvent | Catalyst (Loading wt %) | Temp (° C.) | Pressure (Kg/cm2) | Reaction time (h) | Remarks |
|---|---|---|---|---|---|---|---|
| 50 | 50 | IPA (250 ml) | 10% Rh/C (5 wt % of the Input feed) | 100-110° C. | 14-15 | 6 | NMR shows absence of aromatic peak See FIG. 2A |
| 50 | 50 | IPA (250 ml) | 10% Ru/C (5 wt % of the Input feed) | 100-110° C. | 14-15 | 7.5 | NMR shows absence of aromatic peak |
| 50 | 50 | IPA (250 ml) | 5% Ru/C (1 wt % of the Input feed) | 100-110° C. | 14-15 | 11.5 | NMR shows absence of aromatic peak |
| 100 | 100 | — | 5% Ru/C (2 wt % of the Input feed) | 120-125° C. | 14-15 | 22 | NMR shows absence of aromatic peak See FIG. 2B |

-continued

Figure 2C:
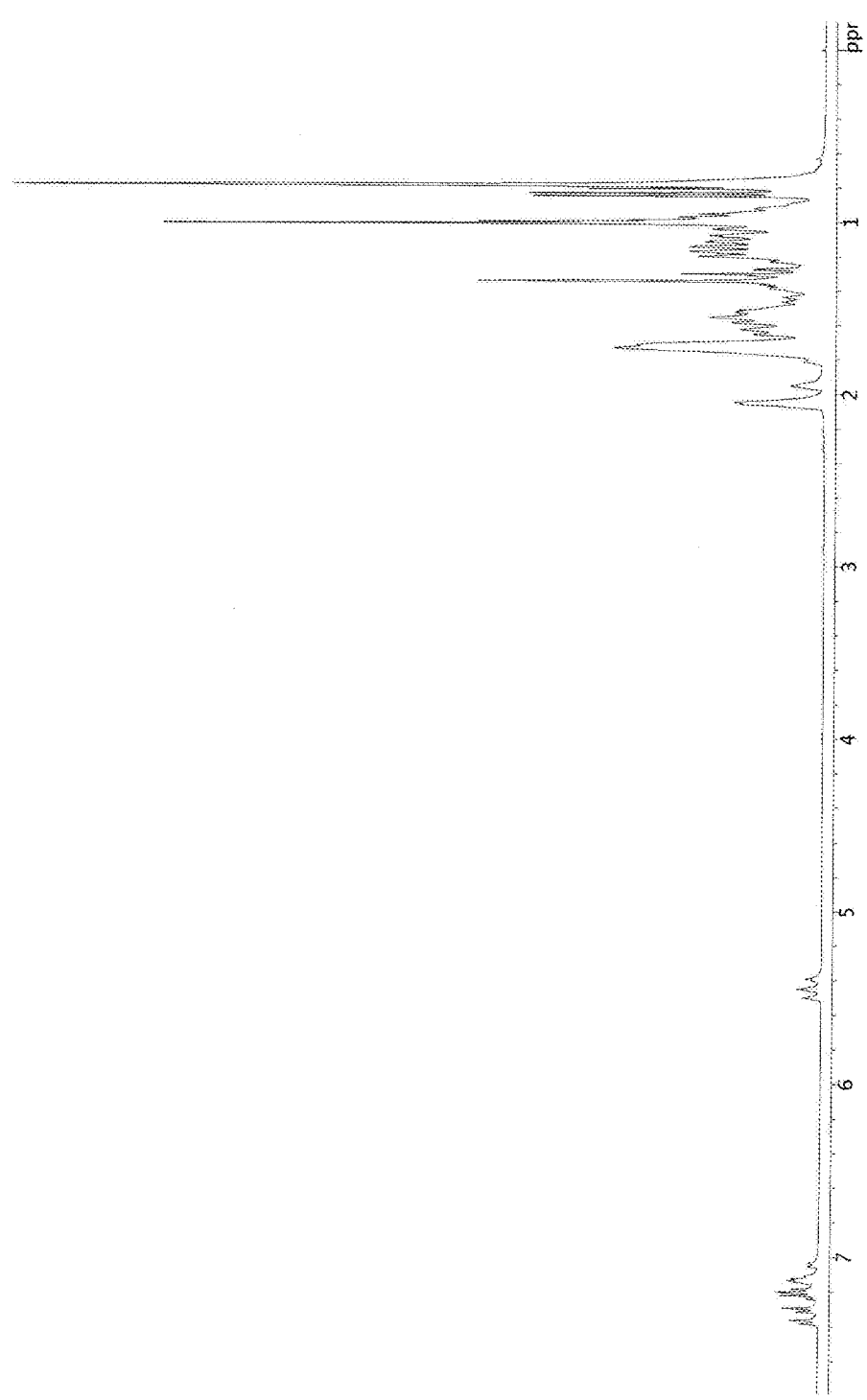

| AMS dimer (g) | Iso-HAD Precursor (g) | Solvent | Catalyst (Loading wt %) | Temp (° C.) | Pressure (Kg/cm2) | Reaction time (h) | Remarks |
|---|---|---|---|---|---|---|---|
| 75 | 75 | — | 5% Ru/C (1 wt% of the Input feed) | 120-125° C. | 14-15 | >22 | NMR show presence of aromatic peaks (Incomplete reaction) See FIG. 2C |

As evidenced by the NMR spectra, FIGS. 2A and 2B, the absence of aromatic peaks indicates completion of the hydrogenation reaction. In contrast, FIG. 2C demonstrates an incomplete reaction. The incomplete reaction of FIG. 2C may be completed by increasing temperature and pressure. Increasing temperature and pressure may also be used to reduce the reaction time.

In the fourth reaction, the HAD precursor acts as solvent and reactant. The HAD precursor is in a liquid state while the iso-HAD precursor is in a solid physical state and a slurry of iso-HAD and HAD was first mixed and then added to the reaction vessel.

Hydrogenation reactions are generally carried out in a polar solvent. Here, the HAD precursor may act as solvent for the iso-HAD. Thus the HAD provides a polar medium, but as it is also a reactant and as the reaction progresses, more HAD is hydrogenated and therefore not able to perform as polar solvent. Without wishing to be bound by theory, it is speculated this is why the reaction is faster in the beginning but as the reaction mixture slowly turns non polar in nature, the reaction slows and thus a reaction time such as 22 hours may be necessary.

Certain embodiments have been described in the form of examples. It is impossible to depict every potential application. Thus, while the embodiments are described in considerable detail, it is not the intention to restrict or in any way limit the scope of the appended claims to such detail, or to any particular embodiment.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. As used in the specification and the claims, the singular forms "a," "an," and "the" include the plural. Finally, where the term "about" is used in conjunction with a number, it is intended to include ±10% of the number. For example, "about 10" may mean from 9 to 11. The term HAD may be used to refer to a hydrogenated alpha dimethyl styrene dimer or hydrogenated dimers of alpha olefins, or any other term referring to the FIGs shown in Formula I or defined as HAD.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:

1. A traction fluid comprising a blend of the molecule of Formula I:

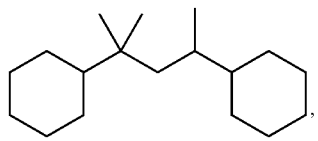

Formula I and
the molecule of Formula II:

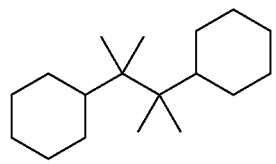

Formula II wherein the blend of Formula I and Formula II is present in an amount between 80 (w/w) % and 99.99 (w/w) %, and
wherein Formula I is present in an amount between 18 (w/w %) and 82 (w/w %) and Formula II is present in an amount between 10 (w/w %) and 75 (w/w %); and, wherein the traction fluid is characterized by a Brookfield viscosity −30° C. between 19,100 cP and 24,000 cP.

2. The traction fluid of claim 1, further comprising one or more additives selected from the group consisting of: anti-foaming agents, antioxidant agents, antiwear agents, extreme pressure agents, detergents, dispersants, anti-rust agents, friction modifiers, corrosion inhibitors, and viscosity modifiers.

3. The traction fluid of claim 2, wherein the additives are present in an amount between 0.01 (w/w) % and 20 (w/w) %.

4. The traction fluid of claim 1, further comprising additives, wherein one additive is a defoaming agent in an amount of 0.1 (w/w) %, a second additive is a viscosity index modifier in an amount of 2 (w/w) %, and a third additive in an amount of 5.7(w/w) %.

5. The traction fluid of claim 1, wherein the blend of Formula I and Formula II is present in an amount between 92 (w/w) % and 94 (w/w) %.

6. The traction fluid of claim 1, wherein Formula I is present in an amount between 23 (w/w) % and 46 (w/w) % and Formula II is present in an amount between about 46 (w/w) % and 70 (w/w) %.

7. The traction fluid of claim 1, wherein a Formula I:Formula II ratio of the traction fluid is between 1:1 and 1:3.

8. The traction fluid of claim 1, wherein the blend of Formula I and Formula II is characterized by:

a viscosity as determined by measurement of Brookfield viscosity @-30° C. that is lower than the viscosity of a traction fluid comprising Formula II as a base fluid alone; or a traction coefficient @ 90° C., 5% SRR, 1.25 GPa equivalent to a traction fluid comprising Formula I as a base fluid alone.

9. The traction fluid of claim 1, wherein the viscosity of the traction fluid blend is 25 to 30% lower than the viscosity of a traction fluid as determined by measurement of Brookfield viscosity @-30° C. comprising Formula II alone; or the traction coefficient @ 90° C., 5% SRR, 1.25 GPa of the traciton fluid blend is within 1% of the traction coefficient of a traction fluid comprising Formula I alone.

10. The traction fluid of claim 1, wherein the fluid is characterized by a Kinematic Viscosity@40° C. between 27.29 cSt and 29.37 cSt.

11. The traction fluid of claim 1, wherein the fluid is characterized by a traction coefficient @ 90° C., 5% SRR, 1.25 GPa between 0.0946 and −0.0948.

\* \* \* \* \*